United States Patent
Aiello

(10) Patent No.: US 11,528,945 B2
(45) Date of Patent: Dec. 20, 2022

(54) MATERNAL UNDER GARMENT

(71) Applicant: Giovanna Aiello, Toronto (CA)

(72) Inventor: Giovanna Aiello, Toronto (CA)

(*) Notice: Subject to any disclaimer, the term of this patent is extended or adjusted under 35 U.S.C. 154(b) by 537 days.

(21) Appl. No.: 16/600,912

(22) Filed: Oct. 14, 2019

(65) Prior Publication Data

US 2021/0106069 A1 Apr. 15, 2021

(51) Int. Cl.
| | |
|---|---|
| *A61F 13/15* | (2006.01) |
| *A41B 9/04* | (2006.01) |
| *A61F 13/72* | (2006.01) |
| *A61F 13/496* | (2006.01) |
| *A61M 35/00* | (2006.01) |
| *A61F 7/10* | (2006.01) |

(52) U.S. Cl.
CPC .............. *A41B 9/04* (2013.01); *A61F 13/496* (2013.01); *A61F 13/72* (2013.01); *A61M 35/10* (2019.05); *A61F 2007/108* (2013.01)

(58) Field of Classification Search
CPC . A41B 9/04; A41B 9/12; A61F 13/496; A61F 13/72; A61F 2007/108; A61F 2013/8414; A61F 13/474; A61F 13/8405; A61F 13/47245; A61F 2013/1517; A61F 2013/4708; A61F 2007/10; A61M 35/10; A41D 1/21

See application file for complete search history.

(56) References Cited

U.S. PATENT DOCUMENTS

| | | | |
|---|---|---|---|
| 6,546,564 B1* | 4/2003 | Palmer | A41B 9/14 2/409 |
| 9,962,286 B2 | 5/2018 | Mahon | |
| 2005/0090796 A1* | 4/2005 | Coleman | A61F 13/622 604/387 |
| 2007/0219515 A1* | 9/2007 | Marsh | A61K 8/0208 516/53 |
| 2009/0036857 A1 | 2/2009 | Sherrod | |

(Continued)

FOREIGN PATENT DOCUMENTS

| | | |
|---|---|---|
| CN | 101313875 A | 12/2008 |
| CN | 203458541 U | 3/2014 |

(Continued)

*Primary Examiner* — Jacqueline F Stephens
(74) *Attorney, Agent, or Firm* — Argus Intellectual Enterprise; Jordan Sworen; Daniel Enea

(57) ABSTRACT

A garment for postnatal women for absorbing postpartum bleeding and providing soothing effects during post-partum recovery. The maternal under garment includes an exterior layer having a waist opening and a pair of leg openings. An interior layer overlaps the exterior layer along a front panel and a rear panel of the garment. An upper perimeter of the front panel includes a V-shape, wherein a nadir of the V-shape is centrally positioned on the front panel to comfortably rest below a stomach area of a woman. The maternal under garment includes an adjustable waist band to retract as the stomach area becomes smaller postpartum. Multiple layers are disposed between the interior and exterior layer, such as an absorbent layer for absorbing postpartum bleeding, a cooling layer for soothing genitals during postpartum recovery, and an antibacterial layer for assisting with pain relief and the healing process after birth.

14 Claims, 4 Drawing Sheets

(56) References Cited

U.S. PATENT DOCUMENTS

2014/0273744 A1* 9/2014 Castellano ............. A41B 17/00
  450/156
2015/0080827 A1* 3/2015 Fogg ....................... A61F 13/84
  604/377
2015/0290049 A1* 10/2015 Riha-Scott ............. A41B 9/001
  604/387

FOREIGN PATENT DOCUMENTS

| CN | 203952455 | * 11/2014 | ............... A41B 9/04 |
| CN | 205667363 | * 11/2016 | ............... A41B 9/04 |
| KR | 100341734 B1 | 10/2003 | |
| WO | 2003099158 A2 | 12/2003 | |

* cited by examiner

MATERNAL UNDER GARMENT

BACKGROUND OF THE INVENTION

The present invention relates to underwear. The present invention provides a maternal under garment configured to absorb fluid and assist in healing and pain relief of a woman postpartum.

After giving birth, women must endure a healing process for several weeks or months thereafter. The process typically includes postpartum vaginal bleeding, vaginal pain at tear cites that occurred during birth or stitched areas where vaginal repair occurred after birth. The process is not only painful and uncomfortable for women, but clothes and undergarments become ruined if appropriate padding is not worn or changed quickly enough when postpartum bleeding occurs.

There have been attempts to address these postpartum issues, such as large absorbent pads to be worn with existing underwear or disposable underwear. However, none of the existing devices provide a garment specifically designed to have a V-shape upper perimeter configured to rest below a postpartum stomach, as well as multiple layers to provide pain relief and healing benefits.

In light of the devices disclosed in the known art, it is submitted that the present invention substantially diverges in design elements and methods from the known art and consequently it is clear that there is a need in the art for an improvement for a maternal under garment. In this regard the instant invention substantially fulfills these needs.

SUMMARY OF THE INVENTION

In view of the foregoing disadvantages inherent in the known types of maternal under garments now present in the known art, the present invention provides a new maternal under garment wherein the same can be utilized for absorbing postpartum bleeding, as well as providing pain relief and assisting in the healing process after giving birth.

It is an objective of the present invention to provide a maternal under garment comprising an exterior layer, an interior layer, a front panel, an opposing rear panel, a first side panel, and an opposing second side panel. The exterior layer comprises a waist opening and a pair of leg openings, wherein the interior layer overlaps the exterior layer along the front panel and rear panel of the garment.

It is another objective of the present invention to provide a maternal under garment wherein an upper perimeter of the front panel includes a V-shape, such that a nadir of the V-shape is centrally positioned on the front panel to comfortably rest below a belly of a woman.

It is yet another objective of the present invention to provide a maternal under garment having an adjustable waist band to retract as the belly becomes smaller postpartum.

It is another objective of the present invention to provide a maternal under garment comprising an absorbent layer and a cooling layer disposed between the exterior and interior layers thereof, wherein the absorbent layer is configured to absorb up to three cups of liquid and the cooling layer comprises a material configured to retain temperature for a length of time.

It is yet another objective of the present invention to provide a maternal under garment having an antibacterial layer comprising an antibacterial liquid, such as witch hazel.

It is therefore an object of the present invention to provide a new and improved new maternal under garment that has all of the advantages of the known art and none of the disadvantages.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings.

Reference will now be made in detail to the exemplary embodiment (s) of the invention. References to "one embodiment," "at least one embodiment," "an embodiment," "one example," "an example," "for example," and so on indicate that the embodiment(s) or example(s) may include a feature, structure, characteristic, property, element, or limitation but that not every embodiment or example necessarily includes that feature, structure, characteristic, property, element, or limitation. Further, repeated use of the phrase "in an embodiment" does not necessarily refer to the same embodiment. Additionally, "garment", "underwear" and "under garment" may be used interchangeably and refer to the present invention.

DETAILED DESCRIPTION OF THE INVENTION

For the purposes of presenting a brief and clear description of the present invention, the preferred embodiment will be discussed as used for receiving detailed item information and allowing a user to quickly locate those items in a store.

Figure 1:
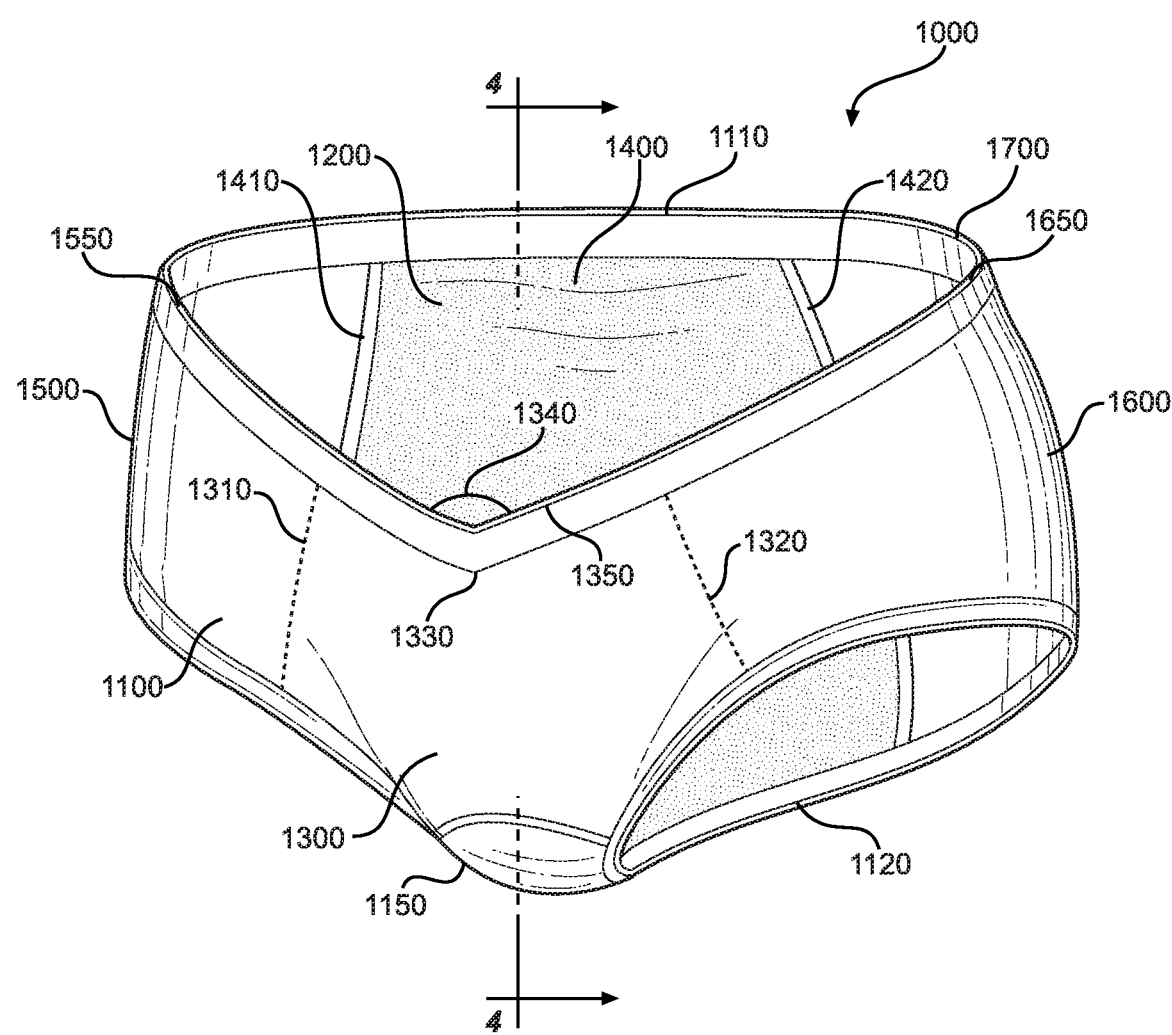
FIG. 1 shows a front perspective view of an embodiment of the maternal under garment.
Figure 2:
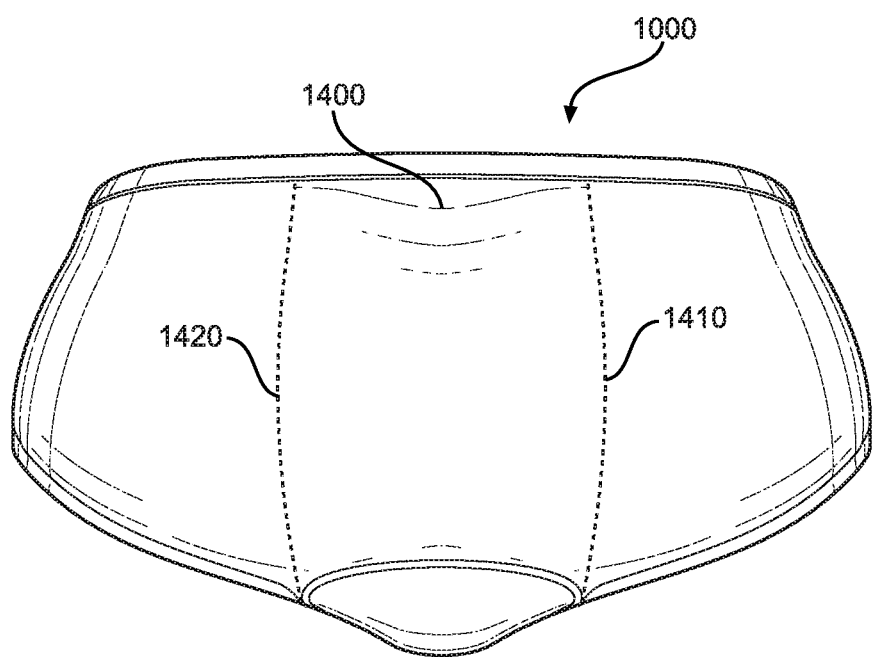
FIG. 2 shows a rear view of a first alternate embodiment of the maternal under garment.

Referring now to FIGS. 1 and 2, there is shown a front perspective view of an embodiment of the maternal under garment and a rear view of a first alternate embodiment of the maternal under garment, respectively. The maternal under garment 1000 is configured to be worn by postnatal women for absorbing postpartum bleeding and providing soothing effects during post-partum recovery. However, in alternate uses, the under garment is adapted to be worn by users seeking to soothe and heal genitals, as well as applications requiring absorption of leakage such as urinary absorption. In the illustrated embodiment, the maternal under garment 1000 comprises a front panel 1300, an opposing rear panel 1400, a first side panel 1500, and an opposing second side panel 1600, wherein each panel forms an exterior layer 1100. An interior layer 1200 is formed along the front panel 1300 and rear panel 1400.

In the illustrated embodiment, the exterior layer 1100 is defined as the outer most layer of the garment 1000 and the interior layer is defined as the interior most layer of the garment configured to directly contact a user's genitals. In the illustrated embodiment, the interior layer 1200 comprises a material configured to allow liquid to pass therethrough, as well as having a smooth surface to prevent the layer 1200 from catching or pulling any stitches of a user when worn.

Figure 3:
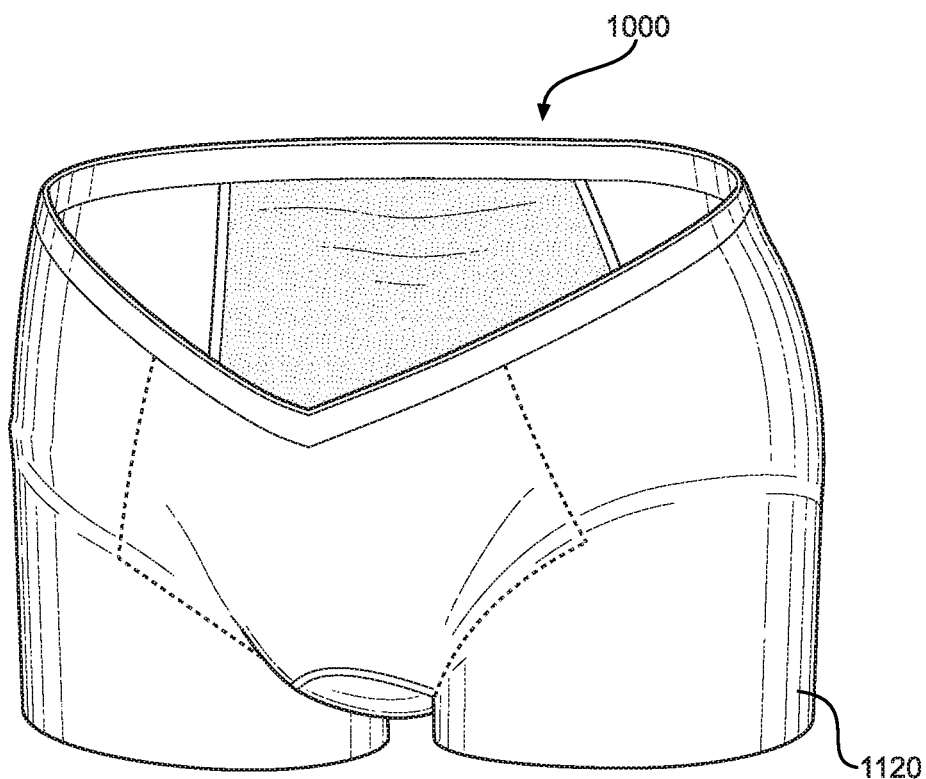
FIG. 3 shows a perspective view of a second alternate embodiment of the maternal under garment.

The exterior layer 1100 is composed of a soft, breathable fabric, such as cotton. In some embodiments, the exterior layer 1100 is biodegradable, organic, includes no added chemicals and is plastic free. The exterior layer 1100 comprises a waist opening 1110 and a pair of leg openings 1120, each configured to receive respective parts of a user's body when donned. In the illustrated embodiment, the leg openings 1120 are configured to rest above a user's thigh when worn. However, in alternate embodiments, as seen in FIG. 3, the leg openings 1120 are configured to extend along a user's thigh when worn. In some embodiments, the maternal under garment 1000 comprises an adjustable waist band 1700 configured to retract as a wearer's stomach area becomes smaller postpartum. In the illustrated embodiment, the adjustable waist band is elastic.

In the illustrated embodiment, the interior layer 1200 only overlaps the exterior layer 1100 along the front and rear panels 1300, 1400, whereas the first and second side panels comprise only the exterior layer. The front panel 1300 extends from a genital region 1150 of the garment toward a front side thereof, whereas the rear panel 1400 extends from the genital region 1150 towards a rear side thereof to form a continuous strip. Opposing lateral sides 1310, 1320 of the front panel 1300 are bounded between the first and second side panels 1500, 1600 and the opposing lateral sides 1410, 1420 of the rear panel 1400 are bounded between the first and second side panels 1500, 1600, such that a lateral side 1310 of the front panel 1300 does not directly engage with a lateral side 1410 of the rear panel 1400.

In the shown embodiment, the uppermost height of the front panel is relatively lower than the uppermost height of the rear panel. An upper perimeter 1350 of the front panel 1300 includes a V-shape, wherein a nadir 1330 of the V-shape is centrally positioned on the front panel 1300 to comfortably rest below a belly of a woman. The nadir is defined as the lowest point. In the illustrated embodiment, the V-shape comprises an angle 1340 between ninety and one hundred and sixty degrees. In some embodiments the upper perimeter 1350 of the front panel 1300 is linear with an adjacent upper perimeter 1550 of the first side panel 1500 or second side panel 1600. However, in alternate embodiments, the upper perimeter 1350 of the V-shape is offset with the perimeter 1550, 1650 of the side panels 1500, 1600.

In the illustrated embodiment, the lateral sides 1310, 1320 of the front panel 1300 and the lateral sides 1410, 1420 of the second panel 1400 taper outwards from the upper perimeter thereof. However, in alternate embodiments, as seen in FIG. 2, the lateral sides 1410, 1420 of the rear panel 1400 of the maternal under garment 1000 are linear or parallel to one another. In this way, the maternal under garment 1000 comprises less interior layer to reduce bulkiness when worn.

Figure 4:
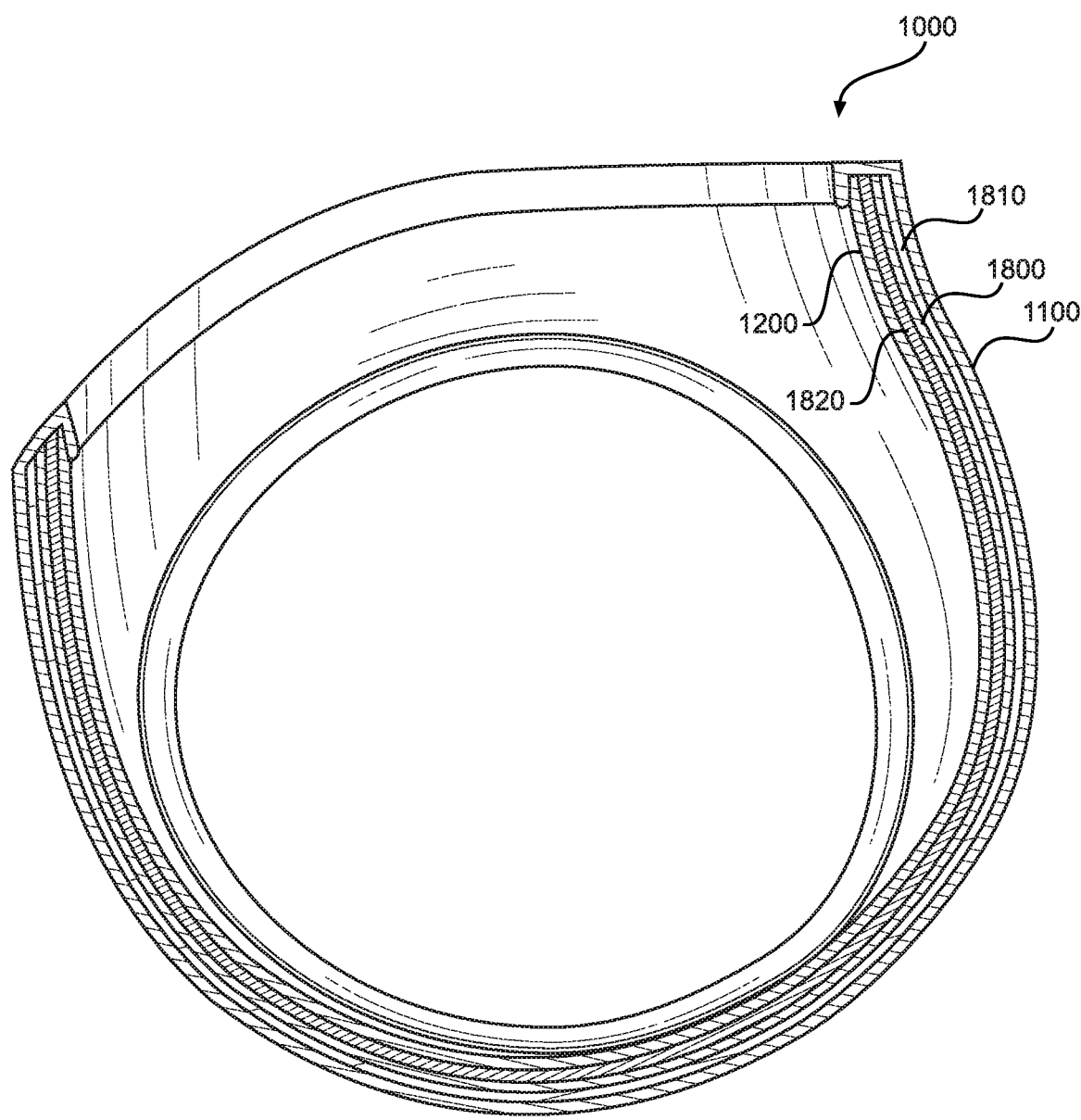
FIG. 4 shows a cross sectional view of an embodiment of the maternal under garment.

Referring now to FIG. 4, there is shown a cross sectional view of an embodiment of the maternal under garment. The maternal under garment 1000 comprises multiple layers sandwiched between the interior layer 1200 and the exterior layer 1100. In the illustrated embodiment, the maternal under garment 1000 comprises an absorbent layer 1800 configured to absorb up to 3 cups of postpartum bleeding. In the illustrated embodiment, the absorbent layer 1800 is not removable and instead embedded between the interior and exterior layer 1100, 1200. The absorbent layer 1800 is composed of any suitable material, such as, but not limited to, cotton.

In some embodiments, the maternal under garment 1000 comprises a cooling layer 1810 configured to provide a soothing effect to the genitals of a user when worn. In the illustrated embodiment, the cooling layer 1810 is disposed closest to the exterior layer 1100, whereas the absorbent layer 1800 is closer to the interior layer 1200 since the cooling layer 1800 is not configured to receive liquid therethrough. In some embodiments, the cooling layer 1810 comprises a cooling gel that can be put in the freezer or refrigerator for lengthening the cooling effect. In other embodiments, the cooling layer 1810 comprises chemicals configured to react with one another to result in a cooling effect. In some embodiments, the cooling layer 1810 is removable through an opening in the exterior layer 1100 in order to replace or refreeze the cooling layer 1810.

In the illustrated embodiment, the maternal under garment 1000 comprises an antibacterial layer 1820 configured to provide pain relief and assist with healing genital sores received from birth. The antibacterial layer 1820 is closest to the interior layer 1200 in order to provide topical relief to the genital area. In the illustrated embodiment, the antibacterial layer 1820 comprises witch hazel embedded onto a substrate similar to the interior layer 1200 that allows postpartum bleeding and other liquid to pass therethrough to the absorbent layer 1800. In some embodiments, the maternal under garment does not have a separate antibacterial layer, but instead an antibacterial liquid is embedded on the interior layer 1200. In the shown embodiment, each layer 1100, 1200, 1800, 1810, 1820 is entirely coextensive with each other layer. Further, each layer 1100, 1200, 1800, 1810, 1820 extends an entirely between an uppermost height of the front panel and the rear panel.

Figure 5:
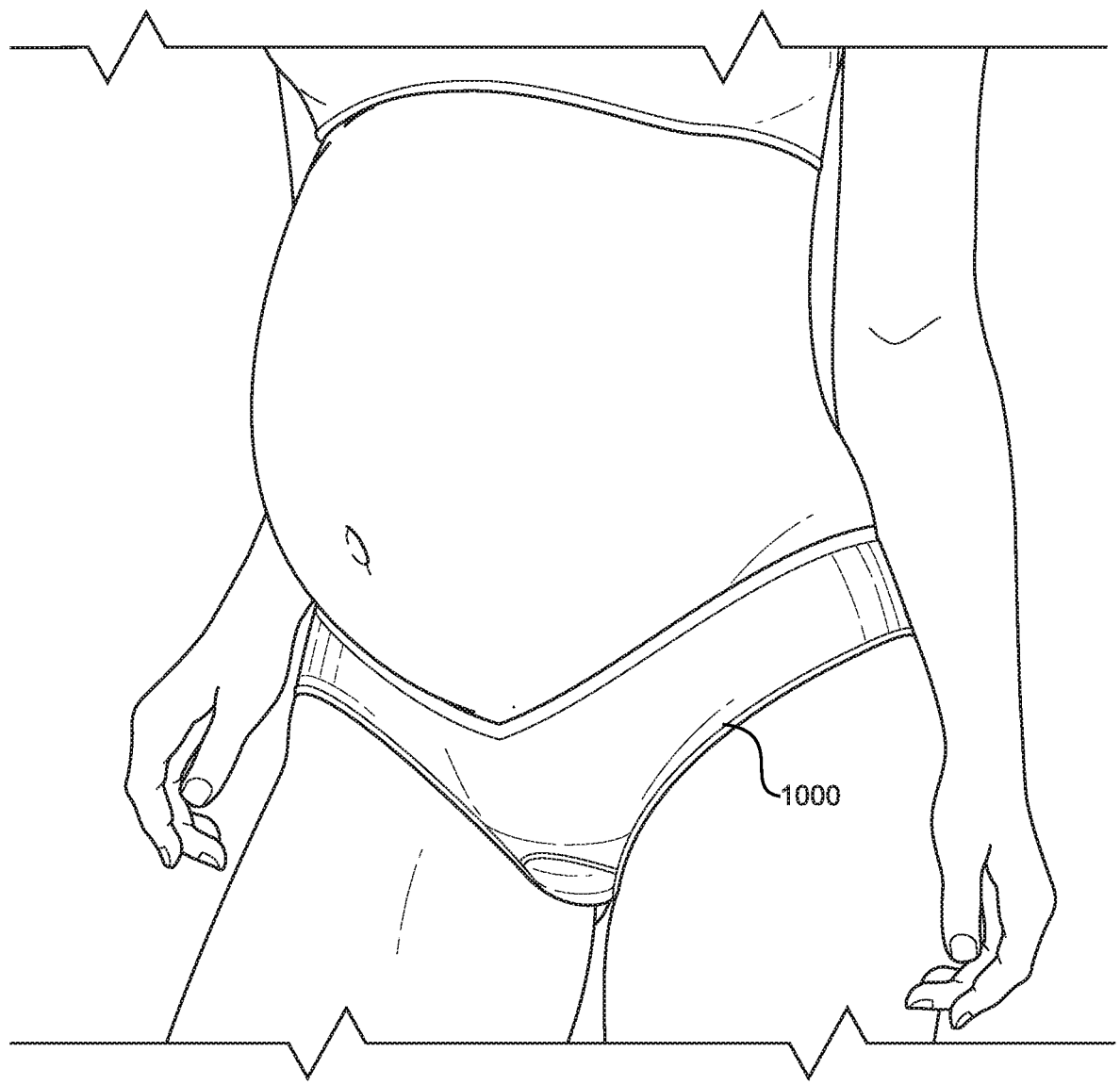
FIG. 5 shows a perspective view of an embodiment of the maternal under garment in use.

Referring now to FIG. 5, there is shown a perspective view of an embodiment of the maternal under garment in use. In operation, the user dons the maternal under garment similar to underwear. Once the maternal under garment is soiled or all of the soothing effects have depleted, such as the witch hazel and cooling effect, the user may change to a new pair of maternal under garment 1000. In some embodiments, the maternal under garment is disposable, whereas in alternated embodiments the maternal under garment is machine washable.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A maternal under garment, comprising:
   a front panel, an opposing rear panel, a first side panel, and an opposing second side panel forming an exterior layer, wherein the first and second side panels are each disposed between the front panel and rear panel;
   wherein the exterior layer comprises a waist opening and a pair of leg openings;
   an interior layer formed along the front panel and the rear panel;
   an absorbent layer positioned between the exterior layer and the interior layer, wherein the exterior, absorbent, and the interior layers are disposed in a stacked configuration:
   wherein the absorbent layer is not removable from the maternal under garment, wherein an upper end of the absorbent layer terminates at the waist opening, such that the absorbent layer extends from an upper end of the front panel to an upper end of the rear panel;
   wherein an upper perimeter of the front panel comprises a V-shape having an angle between 90 and 160 degrees;
   wherein a nadir of the V-shape centrally positioned on the front panel.

2. The maternal garment of claim 1, further comprising an adjustable waist band configured to retract to a small diameter.

3. The maternal garment of claim 1, further comprising a cooling layer having a material configured to provide a cooling effect.

4. The maternal garment of claim 3, wherein the cooling layer comprises a gel configured to be frozen.

5. The maternal garment of claim 3, wherein the cooling layer comprises chemical configured to react with one another to provide a cooling effect.

6. The maternal garment of claim 1, further comprising an antibacterial fluid embedded on the interior layer.

7. The maternal garment of claim 6, wherein the antibacterial fluid is witch hazel.

8. The maternal garment of claim 1, further comprising an antibacterial layer positioned between the interior and exterior layer.

9. The maternal garment of claim 3, wherein the absorbent layer and the cooling layer are coextensive and extends from an upper end of the front panel to an upper end of the rear panel, wherein each layer is disposed in a stacked configuration and the cooling layer is closest to the exterior layer and the absorbent layer is closest to the interior layer.

10. The maternal garment of claim 9, wherein an antibacterial layer is positioned between the interior layer and the absorbent layer.

11. The maternal garment of claim 1, wherein the interior layer only overlaps the exterior layer along the front and rear panels, whereas the first and second side panels comprise only the exterior layer.

12. The maternal garment of claim 1, wherein the front panel and rear panel each comprise opposing lateral sides bounded between the first and second side panels, such that a lateral side of the front panel does not overlap or connect to a lateral side of the rear panel.

13. The maternal garment of claim 12, wherein the opposing lateral sides of the rear panel and the opposing lateral sides of the front panel each taper outward from the upper perimeter thereof.

14. The maternal garment of claim 12, wherein opposing lateral sides of the rear panel are parallel to one another.

* * * * *